United States Patent
Takeshima

(10) Patent No.: US 12,285,247 B2
(45) Date of Patent: Apr. 29, 2025

(54) DATA PROCESSING APPARATUS, DATA PROCESSING METHOD AND MAGNETIC RESONANCE IMAGING APPARATUS

(71) Applicant: Canon Medical Systems Corporation, Otawara (JP)

(72) Inventor: Hidenori Takeshima, Tokyo (JP)

(73) Assignee: Canon Medical Systems Corporation, Otawara (JP)

( * ) Notice: Subject to any disclaimer, the term of this patent is extended or adjusted under 35 U.S.C. 154(b) by 151 days.

(21) Appl. No.: 18/168,789

(22) Filed: Feb. 14, 2023

(65) Prior Publication Data

US 2023/0263422 A1    Aug. 24, 2023

(30) Foreign Application Priority Data

Feb. 18, 2022 (JP) .................. 2022-023997

(51) Int. Cl.
A61B 5/055    (2006.01)

(52) U.S. Cl.
CPC .... *A61B 5/055* (2013.01); *G06T 2207/10088* (2013.01)

(58) Field of Classification Search
CPC .......... A61B 5/055; G06T 2207/10088; G01R 33/4616
See application file for complete search history.

(56) References Cited

U.S. PATENT DOCUMENTS

| | | | | |
|---|---|---|---|---|
| 2011/0087087 A1* | 4/2011 | Peacock, III | ...... | G01R 33/3415 600/410 |
| 2022/0065963 A1* | 3/2022 | Takeshima | ............. | A61B 5/055 |

FOREIGN PATENT DOCUMENTS

| | | |
|---|---|---|
| JP | 2007-159928 A | 6/2007 |
| JP | 2009-291348 A | 12/2009 |

OTHER PUBLICATIONS

Posse et al. MR Spectroscopic Imaging: Principles and Recent Advances, JMRI 37:1301-1325 (Year: 2013).*
Ida, M., et al., Proton MRS Clinical Usefulness Investigative Committee, "Proton MRS Clinical Utility Consensus Guide 2013 edition" Japanese Society for Magnetic Resonance in Medicine Project Research, Jul. 10, 2013, (with English Translation), 167 pages.
Takeshima, H., "Deep Learning and Its Application to Function Approximation for MR in Medicine: An Overview" Magnetic Resonance in Medical Sciences, Sep. 17, 2021, 16 pages.
Mullins, P. G., et al. "Current practice in the use of MEGA-PRESS spectroscopy for the detection of GABA" NEUROIMAGE, vol. 86, pp. 43-52, 2014, 23 pages.

(Continued)

*Primary Examiner* — G.M. A Hyder

(74) *Attorney, Agent, or Firm* — Oblon, McClelland, Maier & Neustadt, L.L.P.

(57) ABSTRACT

According to one embodiment, a data processing apparatus includes processing circuitry. The processing circuitry generates two or more magnetic resonance spectroscopy (MRS) pulse sequences in which different frequency bands are selected as suppression targets. The processing circuitry obtains multiple MRS signals acquired by the two or more MRS pulse sequences. The processing circuitry estimates a relative amount of each molecule included in a measurement target region from the MRS signals, based on a co-occurrence of a frequency profile that depends on a molecule type.

13 Claims, 9 Drawing Sheets

(56) References Cited

OTHER PUBLICATIONS

Harris, A. D. et al., "Edited $^1$H Magnetic Resonance Spectroscopy in Vivo: Methods and Metabolites" Magnetic Resonance in Medicine, vol. 77, issue. 4, pp. 1377-1389, 2017, 29 pages.

\* cited by examiner

| | Band 1 (1.5±0.2) | Band 2 (1.9±0.2) | Band 3 (2.3±0.2) | Band 4 (2.7±0.2) |
|---|---|---|---|---|
| Sequence #1 | on | off | on | off |
| Sequence #2 | off | on | off | on |
| Sequence #3 | on | on | off | on |
| Sequence #4 | on | off | on | on |

FIG. 6

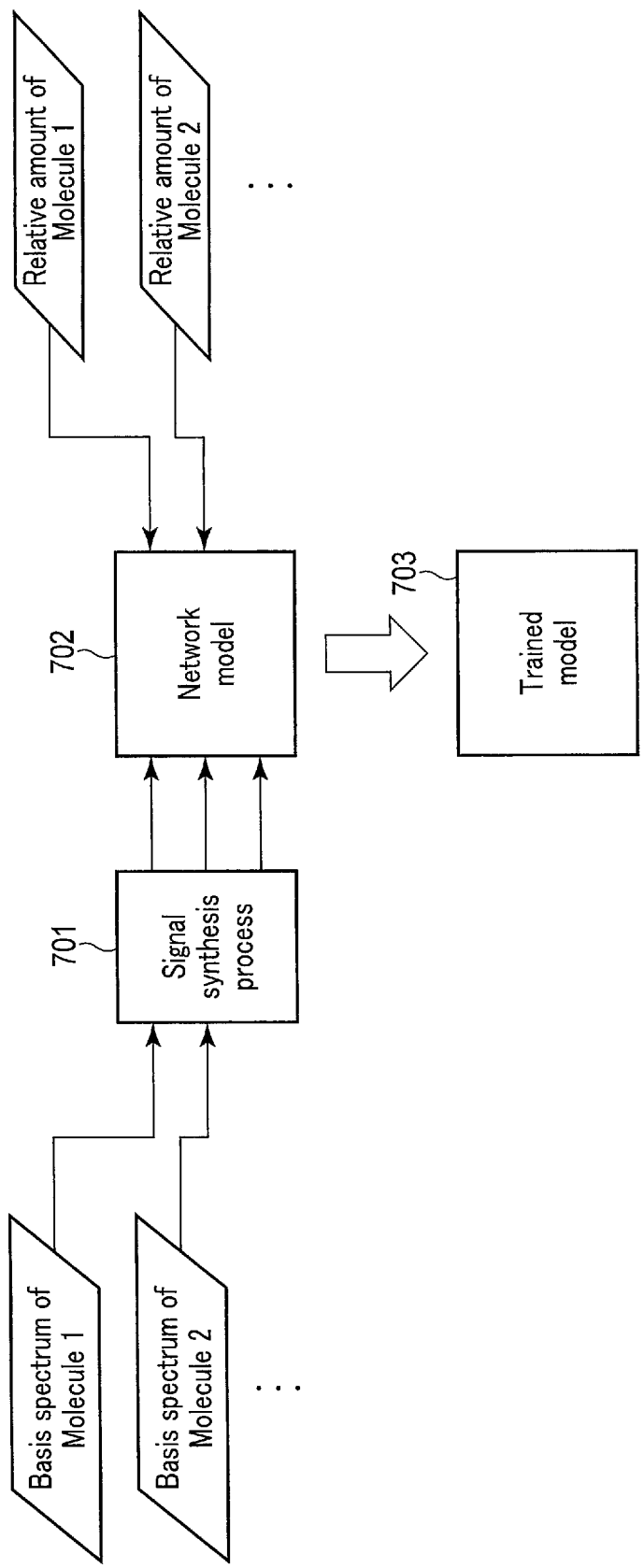
F I G. 7

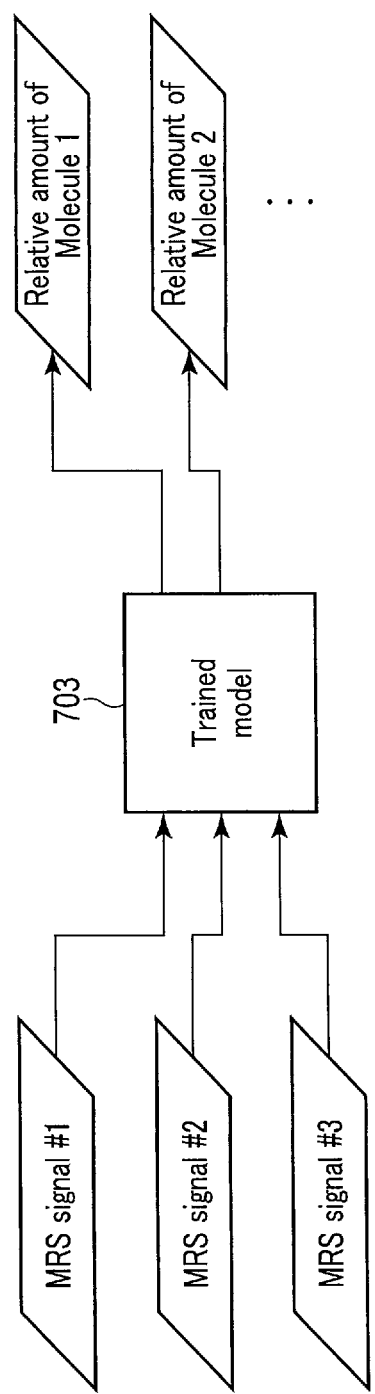
F I G. 8

DATA PROCESSING APPARATUS, DATA PROCESSING METHOD AND MAGNETIC RESONANCE IMAGING APPARATUS

CROSS-REFERENCE TO RELATED APPLICATIONS

This application is based upon and claims the benefit of priority from Japanese Patent Application No. 2022-023997, filed Feb. 18, 2022, the entire contents of which are incorporated herein by reference.

FIELD

Embodiments described herein relate generally to a data processing apparatus, a data processing method and a magnetic resonance imaging apparatus.

BACKGROUND

With magnetic resonance spectroscopy (MRS), it is possible to analyze types of molecules (metabolites) in the body from acquired data. For some types of molecules, a phenomenon called "J-coupling", in which multiple signal peaks appear, may occur. Since each molecule has inherent J-coupling characteristics (also called a "frequency profile"), there is a possibility that the molecule identification properties can be improved by performing signal analysis with the J-coupling taken into consideration.

However, since a large number of molecules with similar chemical shifts exist, if a signal from a molecule is weak, such a signal may be buried by other signals and may not be detected.

BRIEF DESCRIPTION OF THE DRAWINGS

FIG. 6 is a table showing an example of a combination in the case where multiple RF pulses are used.

FIG. 7 is a diagram showing a learning stage of a machine learning model.

FIG. 8 is a diagram showing an inference stage of the machine learning model.

DETAILED DESCRIPTION

In general, according to one embodiment, a data processing apparatus includes processing circuitry. The processing circuitry generates two or more magnetic resonance spectroscopy (MRS) pulse sequences in which different frequency bands are selected as suppression targets. The processing circuitry obtains multiple MRS signals acquired by the two or more MRS pulse sequences. The processing circuitry estimates a relative amount of each molecule included in a measurement target region from the MRS signals, based on a co-occurrence of a frequency profile that depends on a molecule type.

Hereinafter, the data processing apparatus, the data processing method and the magnetic resonance imaging apparatus according to the present embodiment will be described with reference to the drawings. In the embodiments to be described below, elements assigned the same reference symbols are assumed to perform similar operations, and redundant descriptions will be omitted where unnecessary. An embodiment will be described below with reference to the accompanying drawings.

A data processing apparatus according to the present embodiment processes a magnetic resonance signal (hereinafter referred to as an "MR signal") acquired by a magnetic resonance imaging apparatus. The data processing apparatus may be incorporated in the magnetic resonance imaging apparatus, or may be separate from the magnetic resonance imaging apparatus.

Figure 1:
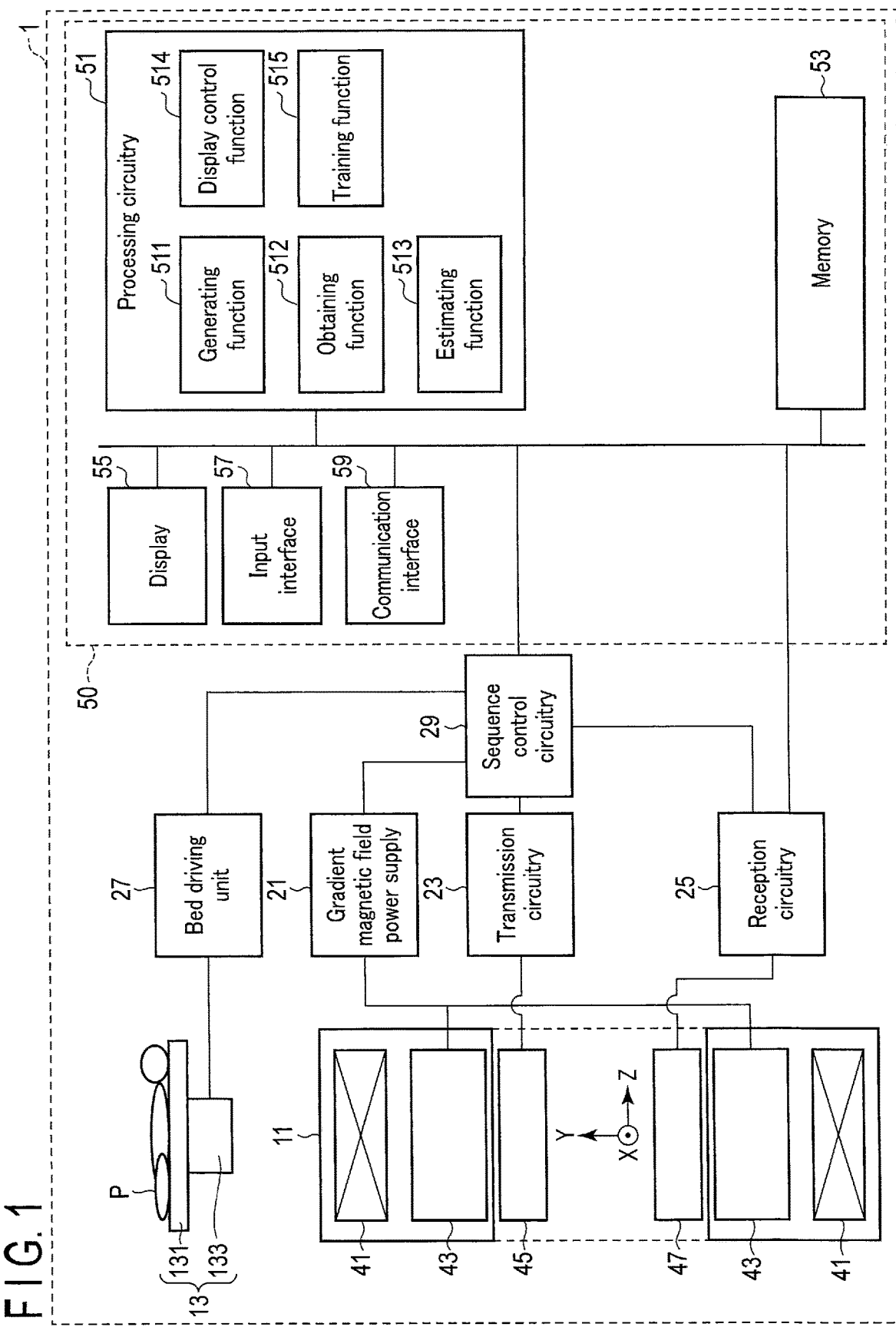
FIG. 1 is a block diagram showing a magnetic resonance imaging apparatus according to the present embodiment.

FIG. 1 is a block diagram showing a configuration example of a magnetic resonance imaging apparatus 1 according to the present embodiment. As shown in FIG. 1, the magnetic resonance imaging apparatus 1 includes a gantry 11, a bed 13, a gradient magnetic field power supply 21, transmission circuitry 23, reception circuitry 25, a bed driving unit 27, sequence control circuitry 29, and a data processing apparatus (host computer) 50.

The gantry 11 includes a static magnetic field magnet 41 and a gradient magnetic field coil 43. The static magnetic field magnet 41 and the gradient magnetic field coil 43 are accommodated in a housing of the gantry 11. A hollow-shaped bore is formed in the housing of the gantry 11. In the bore of the gantry 11, a transmitter coil 45 and a receiver coil 47 are disposed.

The static magnetic field magnet 41 has a hollow, substantially cylindrical shape, and produces a static magnetic field in the interior of the substantial cylinder. Examples of the static magnetic field magnet 41 that may be used include a permanent magnet, a superconducting magnet, a normal conducting magnet, etc. It is assumed that the central axis of the static magnetic field magnet 41 is defined as a Z axis, that an axis vertically orthogonal to the Z axis is defined as a Y axis, and that an axis horizontally orthogonal to the Z axis is defined as an X axis. The X, Y, and Z axes configure an orthogonal three-dimensional coordinate system.

The gradient magnetic field coil 43 is a coil unit attached to the inside of the static magnetic field magnet 41 and formed in a hollow, substantially cylindrical shape. The gradient magnetic field coil 43 produces a gradient magnetic field upon receiving a current supply from the gradient magnetic field power supply 21. More specifically, the gradient magnetic field coil 43 includes three coils that respectively correspond to the X, Y, and Z axes and are orthogonal to one another. The three coils respectively form, along the X, Y, and Z axes, gradient magnetic fields with varying magnetic field intensities.

The gradient magnetic fields respectively formed along the X, Y, and Z axes are synthesized, and a slice selective gradient magnetic field Gs, a phase encoding gradient magnetic field Gp, and a frequency encoding gradient magnetic field Gr, which are orthogonal to one another, are formed in desired directions. The slice selective gradient magnetic field Gs is employed to freely determine an imaging slice. The phase encoding gradient magnetic field Gp is employed to vary the phase of a magnetic resonance signal (hereinafter referred to as an "MR signal") in accordance with the spatial position. The frequency encoding gradient magnetic field Gr is employed to vary the frequency of an MR signal in accordance with the spatial position. In the description that follows, it is assumed that the direction of the gradient of the slice selective gradient magnetic field Gs is the Z axis, that the direction of the gradient of the phase encoding gradient magnetic field Gp is the Y axis, and that the direction of the gradient of the frequency encoding gradient magnetic field Gr is the X axis.

The gradient magnetic field power supply 21 supplies a current to the gradient magnetic field coil 43 in accordance with a sequence control signal from the sequence control circuitry 29. By supplying the current to the gradient magnetic field coil 43, the gradient magnetic field power supply 21 causes the gradient magnetic field coil 43 to produce gradient magnetic fields along the X, Y, and Z axes. The gradient magnetic fields are superimposed on the static magnetic fields formed by the static magnetic field magnet 41, and are applied to the object P.

The transmitter coil 45 is, for example, disposed inside the gradient magnetic field coil 43, and produces a radiofrequency pulse (hereinafter referred to as an "RF pulse") in response to a current supply from the transmission circuitry 23.

The transmission circuitry 23 supplies a current to the transmitter coil 45 to apply, to an object P via the transmitter coil 45, an RF pulse for exciting a target proton existing in the object P. The RF pulse oscillates at a resonant frequency inherent in the target proton, and excites the target proton. An MR signal is generated from the excited target proton, and is detected by the receiver coil 47. The transmitter coil 45 is, for example, a whole-body coil (WB coil). The whole-body coil may be used as a transmitter/receiver coil.

By the action of the RF pulse, the receiver coil 47 receives the MR signal issued from the target proton existing in the object P. The receiver coil 47 includes a plurality of receiver coil elements configured to receive an MR signal. The received MR signal is supplied to the reception circuitry 25 in a wired or wireless manner. Although not illustrated in FIG. 1, the receiver coil 47 includes a plurality of receiver channels provided in a parallel manner. Each receiver channel includes a receiver coil element configured to receive an MR signal, an amplifier configured to amplify the MR signal, and the like. The MR signal is output for each receiver channel. The total number of receiver channels may be equal to, greater than, or smaller than the total number of receiver coil elements.

The reception circuitry 25 receives the MR signal generated from the excited target proton via the receiver coil 47. The reception circuitry 25 signal-processes the received MR signal, and generates a digital MR signal. A digital MR signal can be expressed in a k-space defined by a spatial frequency. Accordingly, a digital MR signal will be hereinafter referred to as "k-space data". The k-space data is an example of an MR acquisition signal. The k-space data is supplied to the data processing apparatus 50 in a wired or wireless manner.

The transmitter coil 45 and the receiver coil 47 are described merely as examples. Instead of the transmitter coil 45 and the receiver coil 47, a transmitter/receiver coil equipped with both a transmitting function and a receiving function may be used. Also, the transmitter coil 45, the receiver coil 47, and the transmitter/receiver coil may be combined.

The bed 13 is installed adjacent to the gantry 11. The bed 13 includes a top 131 and a base 133. The object P is mounted on the top 131. The base 133 slidably supports the top 131 along each of the X, Y, and Z axes. The bed driving unit 27 is accommodated in the base 133. The bed driving unit 27 moves the top 131 under control of the sequence control circuitry 29. The bed driving unit 27 may include, for example, any motor such as a servomotor, a stepping motor, etc.

The sequence control circuitry 29 includes, as hardware resources, a processor such as a central processing unit (CPU) or a micro processing unit (MPU) and a memory such as a read-only memory (ROM) or a random-access memory (RAM). The sequence control circuitry 29 acquires k-space data relating to the object P by synchronously controlling the gradient magnetic field power supply 21, the transmission circuitry 23, and the reception circuitry 25 based on data acquisition conditions set by a generating function 511 of the processing circuitry 51, and performing data acquisition on the object P according to the data acquisition conditions. The sequence control circuitry 29 is an example of a sequence control unit.

The sequence control circuitry 29 according to the embodiment executes data acquisition for MR spectroscopy (hereinafter also referred to "MRS"), which is a type of chemical shift measurement. The chemical shift measurement is a technique of measuring a chemical shift, which is a small difference in the resonant frequency of target protons such as hydrogen nuclei caused by differences in the chemical environment. The MRS includes a single voxel technique in which data is acquired for a single voxel and a multi-voxel technique in which data is acquired for multiple voxels, and the present embodiment is applicable to both of these techniques. The multi-voxel technique is also referred to as chemical shift imaging (CSI), MRS imaging (MRSI), etc. The voxel of the measurement target region is referred to as a "voxel of interest".

The sequence control circuitry 29 executes data acquisition for MRS on the object P. By executing data acquisition for MRS, a free induction decay (FID) signal or a spin echo signal is generated from a voxel of interest of the object P. The reception circuitry 25 receives an FID signal or a spin echo signal via the receiver coil 47, signal-processes the received FID signal or spin echo signal, and acquires k-space data relating to the voxel of interest. It is assumed that the acquired k-space data is digital data representing the intensity value of a signal issued from the voxel of interest as a time function. A pulse sequence for MRS is repeated by the number of excitations (NEX), and k-space data corresponding to the NEX is acquired. The k-space data acquired by MRS is referred to as "MRSk data". The MRSk data is an example of an MRS signal.

As shown in FIG. 1, the data processing apparatus 50 is a computer including processing circuitry 51, a memory 53, a display 55, an input interface 57, and a communication interface 59.

The processing circuitry 51 includes a processor such as a CPU as a hardware resource. The processing circuitry 51 functions as the nerve of the magnetic resonance imaging apparatus 1. The processing circuitry 51 implements, for example, a generating function 511, an obtaining function 512, an estimating function 513, a display control function 514, and a training function 515 by executing various programs.

Through the generating function 511, the processing circuitry 51 generates two or more MRS pulse sequences for which frequency bands selected as suppression targets differ. The MRS pulse sequences are set either automatically or manually. Specifically, pulse sequences including frequency selection pulses corresponding to different frequency profiles are used as an example of the MRS pulse sequences. For the MRS pulse sequences, techniques such as point resolved spectroscopy (PRESS), stimulated echo acquisition mode (STEAM), semi-localization by adiabatic selective refocusing (semi-LASER), LASER, etc. are known.

In the present embodiment, MRS-related data acquisition conditions are also set. Example items of the MRS-related data acquisition conditions include, as well as the above-described MRS pulse sequences, a repetition time (TR), an echo time (TE), an NEX, a spectrum width, a sampling number, a data acquisition method, a region selection pulse, etc.

For example, the processing circuitry 51 generates, based on the MRSk data, a spectrum (hereinafter referred to as an "MRS spectrum") indicating a signal intensity for each chemical shift. The MRS spectrum is an example of an MRS signal.

Through the obtaining function 512, the processing circuitry 51 obtains multiple MRS signals respectively acquired by two or more MRS pulse sequences.

Through the estimating function 513, the processing circuitry 51 estimates a relative amount (relative intensity) of each molecule included in a measurement target region from multiple MRS signals, based on a co-occurrence of the frequency profile that depends on the type of molecule (metabolite). The frequency profile that depends on the type of molecule is a chemical shift value inherent in each molecule, and corresponds to a peak position on the MRS spectrum. For example, each metabolite includes one or more inherent chemical shift values.

If a trained model is applied, the processing circuitry 51 causes, through the display control function 514, a screen to display one or more predetermined frequency band candidates for selection. If a trained model is not applied, the processing circuitry 51 causes, through the display control function 514, a screen to display one or more frequency band candidates that allow for data reconstruction for selection.

Through the training function 515, the processing circuitry 51 trains a model using training data, and generates a trained model. The training data and the learning method will be described later.

The memory 53 is a storage device configured to store a variety of information, such as a hard disk drive (HDD), a solid-state drive (SSD), an integrated circuit memory device, etc. The memory 53 may also be a drive, etc. configured to read and write a variety of information to and from a CD-ROM drive, a DVD drive, a portable storage medium such as a flash memory, etc. The memory 53 stores, for example, a substance quantity estimation NN, a data acquisition condition, an MRS signal, a control program, etc.

The display 55 displays, through the display control function 514, a variety of information. For the display 55, a CRT display, a liquid crystal display, an organic EL display, an LED display, a plasma display, or any other display known in the present technical field, for example, may be suitably employed.

The input interface 57 includes an input device that accepts various instructions from the user. For the input device, a keyboard, a mouse, various types of switches, a touch screen, a touch pad, etc. may be employed. The input device is not limited to a device including physical operational components, such as a mouse and a keyboard. Examples of the input interface 57 include electrical signal processing circuitry configured to receive an electrical signal corresponding to an input operation from an external input device provided separately from the magnetic resonance imaging apparatus 1 and output the received electrical signal to various circuits. The input interface 57 may be a speech recognition device configured to convert an audio signal acquired by a microphone into an instruction signal.

The communication interface 59 is an interface configured to connect, via a local area network (LAN), etc., the magnetic resonance imaging apparatus 1 with a work station, a picture archiving and communication system (PACS), a hospital information system (HIS), a radiology information system (RIS), and the like. The communication interface 59 transmits and receives various types of information to and from the work station, the PACS, the HIS, and the RIS to which the communication interface 59 is connected.

Figure 2:
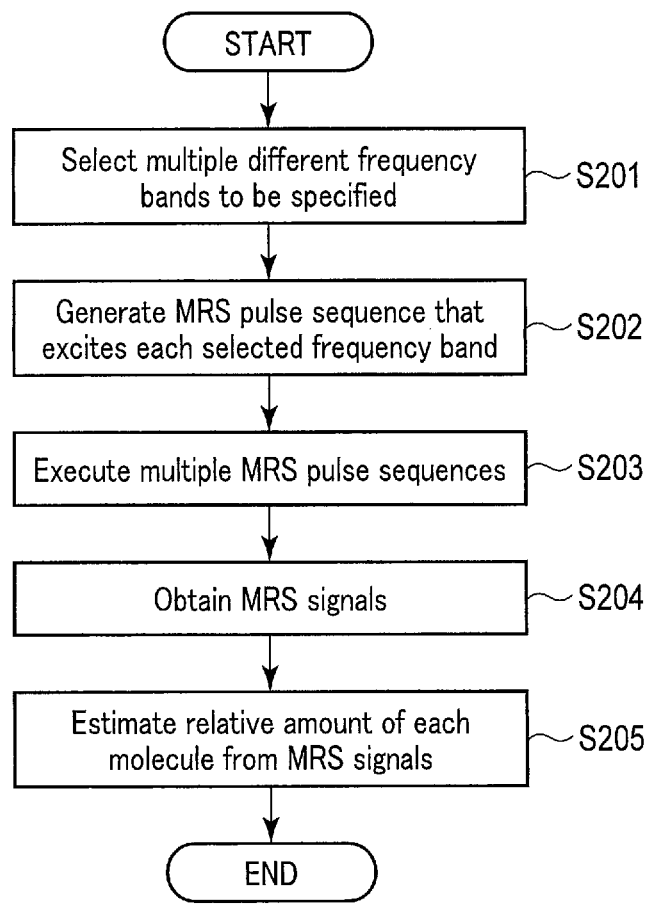
FIG. 2 is a flowchart showing an operation of the magnetic resonance imaging apparatus including a data processing apparatus.

Next, an operation example of the magnetic resonance imaging apparatus 1 including the data processing apparatus 50 according to the present embodiment will be described with reference to the flowchart of FIG. 2.

At step S201, the processing circuitry 51 selects, as suppression targets, multiple different frequency bands to be excited based on an MRS pulse sequence. For example, the processing circuitry 51 may be configured to accept, through the display control function 514, an input or selection of multiple different frequency bands from a user. Alternatively, the processing circuitry 51 may be configured to select, through the generating function 511, predetermined multiple different frequency bands.

At step S202, the processing circuitry 51 generates, through the generating function 511, an MRS pulse sequence for each of the frequency bands selected as the suppression targets.

At step S203, the sequence control circuitry 29 repeatedly executes multiple MRS pulse sequences in order, and acquires an MRS signal for each of the MRS pulse sequences. The number of repetitions of the MRS pulse sequences is determined based on, for example, a NEX of the MRS signal.

At step S204, the processing circuitry 51 obtains, through the obtaining function 512, multiple MRS signals acquired for the respective MRS pulse sequences. At step S205, through the estimating function 513, the processing circuitry 51 estimates a relative amount of each of the molecules included in the measurement target region from the obtained multiple MRS signals. An estimation process can be performed by, for example, inputting the multiple MRS signals to the trained model, thereby obtaining an estimation result of the relative amount of each molecule from the trained model.

Next, a first example of an MRS pulse sequence assumed in the present embodiment will be described with reference to FIG. 3.

Figure 3:
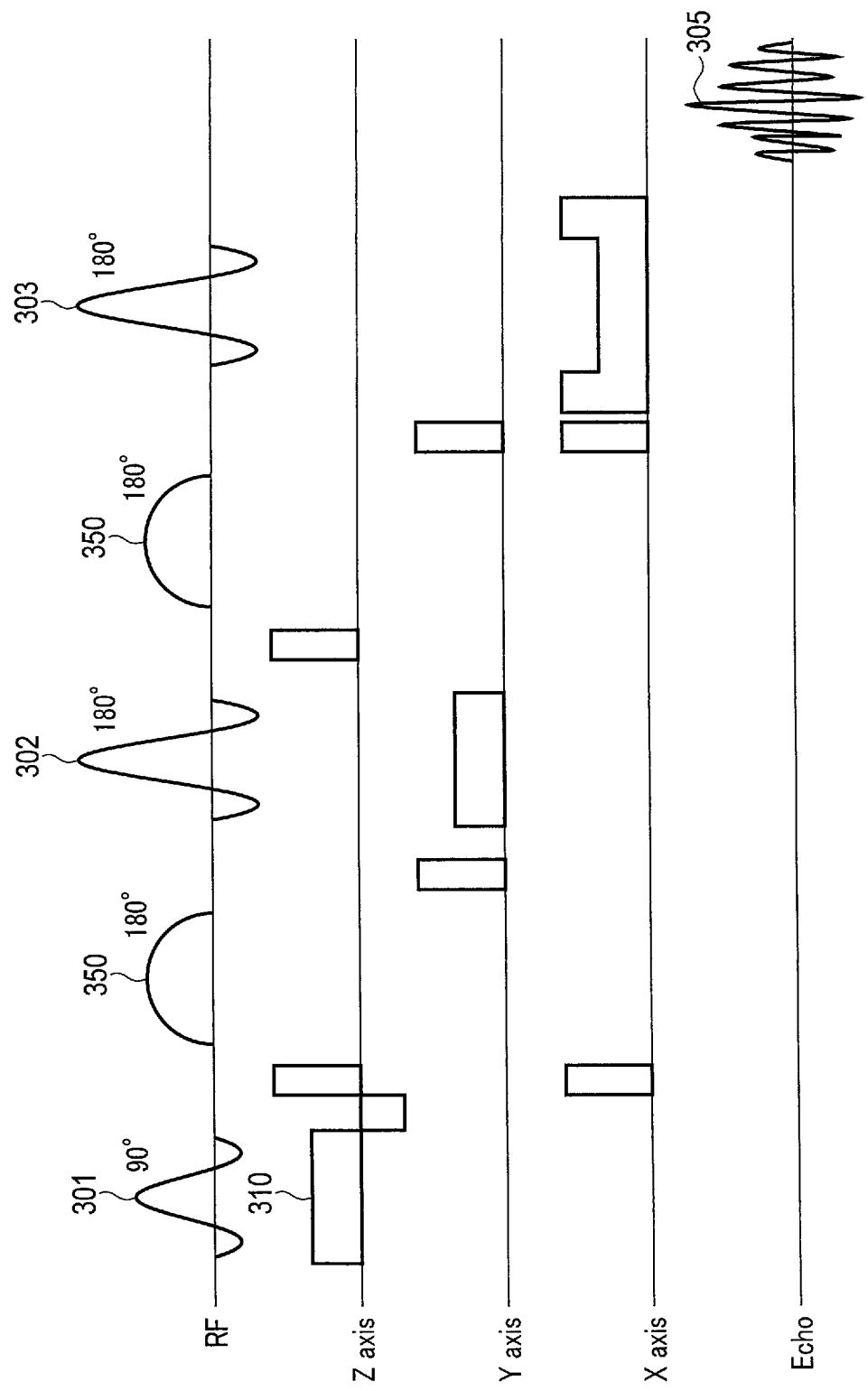
FIG. 3 is a diagram showing a first example of MRS pulse sequences.

FIG. 3 is an MRS pulse sequence diagram based on a MEGA-PRESS technique (Non-Patent Document: M. Mescher et al., Solvent Suppression Using Selective Echo Dephasing. J. Magnetic Resonance Series A 123, Article No. 0242, 226-229 (1996)).

MEGA pulses, which are frequency selection pulses, are applied between three-time RF-pulse irradiations by the PRESS technique. In the example of FIG. 3, by applying a gradient magnetic field 310 along a Z-axis, an excitation pulse 301 (90-degree pulse) is applied while selecting a slice plane in a Z-axis direction. Thereafter, by applying a MEGA pulse 350 (180-degree pulse) and then applying a gradient magnetic field 310 along a Y axis, a refocusing pulse 302 (180-degree pulse) is applied while selecting a slice plane in a Y-axis direction. Thereafter, by applying a MEGA pulse 350 (180-degree pulse) and then applying a gradient magnetic field 310 along an X axis, a refocusing pulse 303 (180-degree pulse) is applied while selecting a slice plane in an X-axis direction. The reception circuitry 25 is configured to receive an echo signal 305 generated from the measurement target region, which is a voxel selected through the above-described operations, as an MRS signal.

Also, in the case of imaging without frequency band selection, the MEGA pulse 350 is not applied, and a sequence based on a normal PRESS technique, namely, an excitation pulse 301, a refocusing pulse 302, and a refocusing pulse 303 are sequentially applied.

A case has been described where a MEGA-PRESS technique is used with reference to FIG. 3; however, a STEAM, semi-LASER, or LASER technique, for example, may be used instead of the PRESS technique.

Next, a second example of the MRS pulse sequences according to the present embodiment will be described with reference to FIG. 4.

Figure 4:
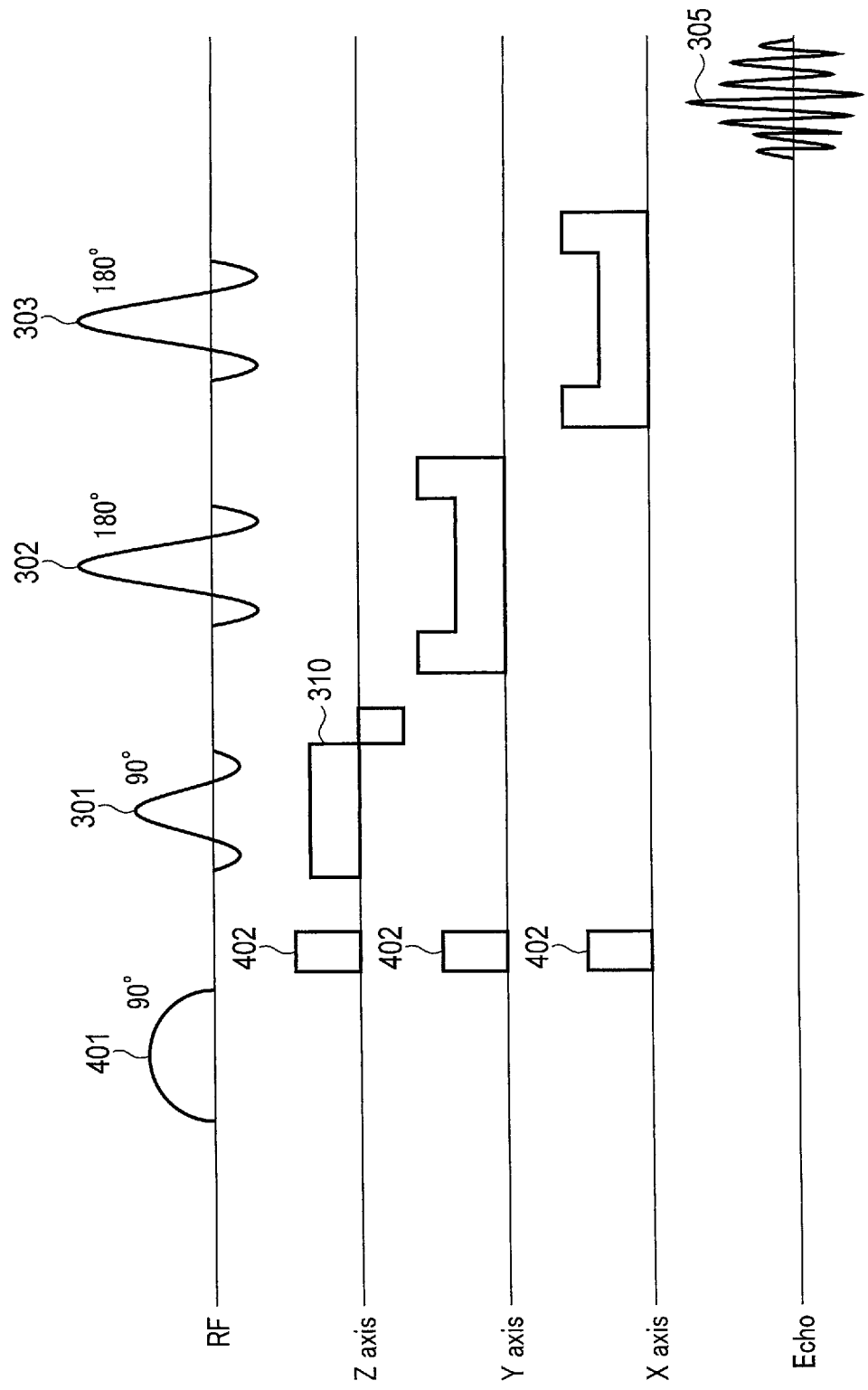
FIG. 4 is a diagram showing a second example of the MRS pulse sequences.

In FIG. 4, prior to an excitation pulse 301, a 90-degree pulse is applied as a pre-pulse 401 relating to frequency selection equivalent to the MEGA pulse 350. Also, a gradient magnetic field 402, which functions as a crasher for eliminating transverse magnetization, is applied in each axis. For a portion of the pulse sequence other than the MEGA pulse, a pulse sequence based on a general PRESS technique may be used.

In both of FIGS. 3 and 4, a process for suppressing signals such as water and fat may be executed. For example, RF pulses at frequencies corresponding to the peaks of water and fat may be applied as pre-pulses. In FIGS. 3 and 4, the MRS pulse sequences are assumed to be based on a PRESS technique; however, other pulse sequences based on, for example, STEAM, semi-LASER, and LASER techniques may also be adopted.

Next, an example of frequency bands selected as suppression targets in MRS pulse sequences will be described with reference to FIG. 5.

Figure 5:
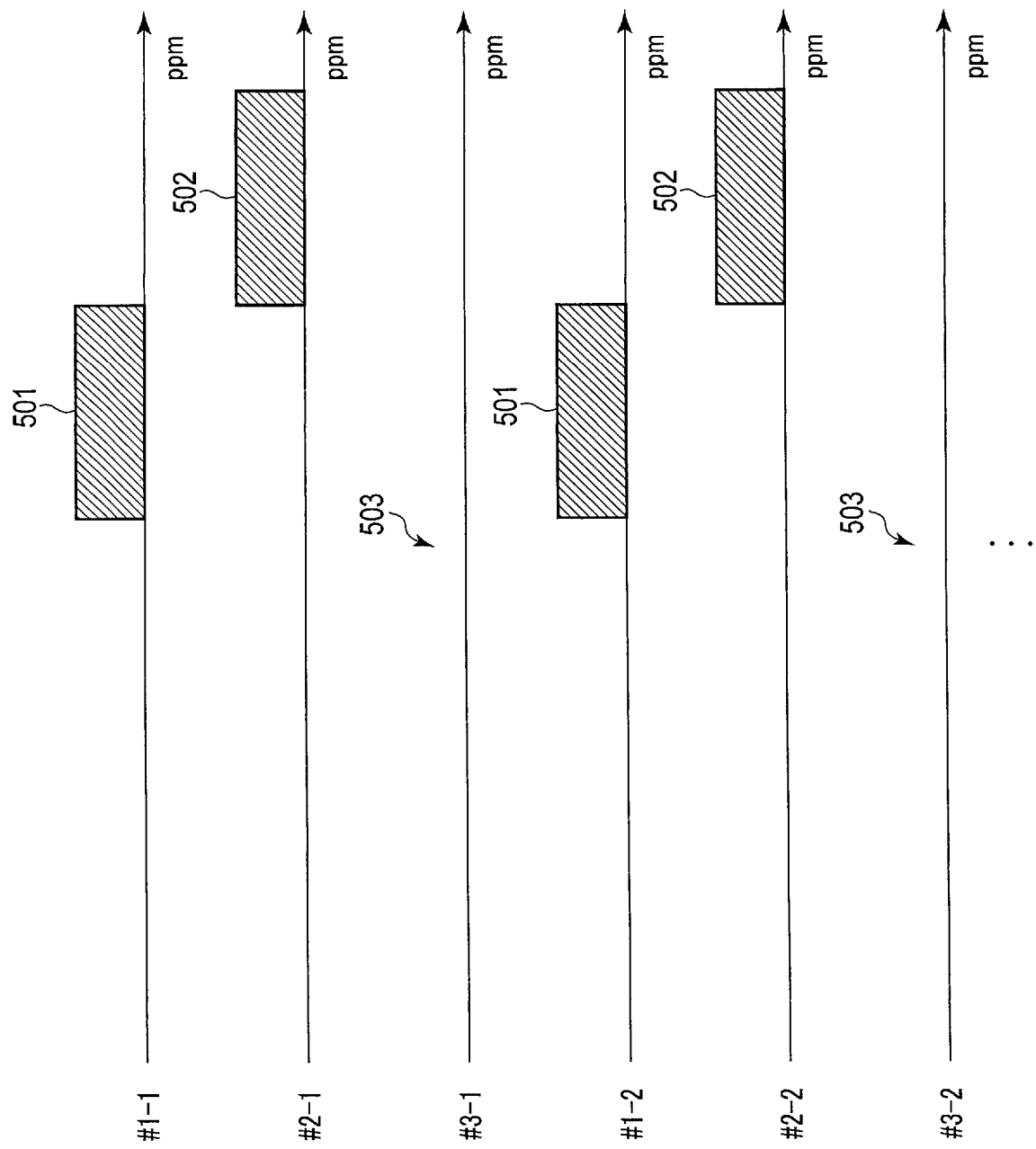
FIG. 5 is a diagram showing an example of frequency bands selected as suppression targets in MRS pulse sequences.

FIG. 5 shows frequency bands respectively selected as suppression targets in two MRS pulse sequences and frequency bands relating to MRS pulse sequences in which a frequency band is not selected. In the examples of FIG. 5 and thereafter, a set of three MRS pulse sequences is repeated, and an MRS signal is obtained for each of the three MRS pulse sequences; however, the configuration is not limited thereto, and MRS pulse sequences in which two or more different frequency bands are selected as suppression targets may configure a single set, and two or more MRS signals corresponding to each MRS pulse sequence may be acquired.

The MRS pulse sequences shown in FIGS. 3 and 4 are pulse sequences relative to a time TR (repetition time) for obtaining a single MR signal for which only a band of a MEGA-based frequency selection pulse corresponding to a frequency profile of a molecule is suppressed. If three different frequency bands are suppressed, the MRS pulse sequences shown in FIGS. 3 and 4 may be set for each frequency band selected as a suppression target, and multiple sets of three MRS pulse sequences may be repeated by the number of exitations. One of the MRS pulse sequences included in a single set may be an MRS pulse sequence relating to a broad frequency band, in which a specific frequency selection pulse is not selected as a suppression target.

Specifically, in the example of FIG. 5, an MRS pulse sequence #1-1 in which the first frequency band 501 is suppressed, an MRS pulse sequence #2-1 in which a second frequency band 502 different from the first frequency band 501 is suppressed, and an MRS pulse sequence #3-1 in which a MEGA pulse is turned off and a frequency band as a suppression target is not selected (in other words, a broad frequency band 503 is specified) are sequentially executed. Thereafter, subsequent to acquisition of the MRS pulse sequence #3-1, a second set is executed, with a single set being MRS pulse sequences #1 to #3. That is, MRS pulse sequences are repeated for each set, in the order of, for example, an MRS pulse sequence #1-2 in which the first frequency band 501 is suppressed, an MRS pulse sequence #2-2 in which the second frequency band 502 is suppressed, and an MRS pulse sequence #3-2 in which a MEGA pulse is turned off.

A single set may be configured of an MRS pulse sequence in which a frequency band different from the first frequency band 501 and the second frequency band 502 is selected as a suppression target, instead of an MRS pulse sequence in which the broad frequency band 503 is specified.

In an MRS pulse sequence in which the broad frequency band 503 is specified, a pulse that suppresses at least one of water and fat may be included. That is, a "broad frequency band" in the present embodiment may be a frequency band from which only bands corresponding to the peaks of water and fat are selectively suppressed (e.g., centered around 4.8 ppm and 1.3 ppm).

An MRS signal is generated by adding MRS signals acquired in the respective MRS pulse sequences. That is, an MRS signal of MRS pulse sequence #1 is generated by adding N signals of MRS pulse sequences #1-1, 1-2, . . . , and 1-N. The same applies to the MRS pulse sequence #2 and the MRS pulse sequence #3. Thereby, deviations in MRS signals caused by body movement, etc. can be averaged.

In MRS pulse sequences in which an identical frequency band is acquired, excitation pulses with different phases may be used. For example, the phase of the excitation pulse is varied in such a manner that an excitation pulse with a zero-degree phase is applied in the first MRS pulse sequence #1-1, an excitation pulse with a 90-degree phase is applied in the second MRS pulse sequence #1-2, and an excitation pulse with a 180-degree phase is applied in the first MRS pulse sequence #1-3.

The phase of the excitation pulse may be varied among MRS pulse sequences in a single set in which different frequency bands are selected as suppression targets. For example, the phase of the excitation pulse may be varied in such a manner that an excitation pulse with a zero-degree phase is applied in the MRS pulse sequence #1-1, an excitation pulse with a 90-degree phase is applied in the MRS pulse sequence #2-1, and an excitation pulse with a 180-degree phase is applied in the MRS pulse sequence #3-1. Moreover, excitation pulses with different phases may be used in both of the MRS pulse sequences in a single set in which an identical frequency band is acquired, and the MRS pulse sequences in a single set in which different frequency bands are selected as suppression targets.

Furthermore, the frequency bands of the MRS pulse sequences #1 to #3 in a single set may partially overlap one another. Specifically, the first frequency band 501 may be "1.3 ppm±0.6 ppm", and the second frequency band 502 may be "1.7 ppm±0.6 ppm". In this case, overlapping occurs in the band of "1.1 ppm to 1.9 ppm".

In the above-described MRS pulse sequences, a case is assumed where a single frequency band is selected as a suppression target; however, multiple frequency bands selected as suppression targets may be synthesized (encoded).

An example of a combination in the case where multiple frequency bands are selected as suppression targets will be described with reference to FIG. 6.

In the table shown in FIG. 6, the columns represent MRS pulse sequences (simply referred to as "sequences" in the description of FIG. 6), and the rows represent frequency bands selected as suppression targets. For example, in a sequence #1, two bands including a band 1 (1.5 ppm±0.2 ppm) and a band 3 (2.3 ppm±0.2 ppm) are selected as suppression targets. In a sequence #3, three bands including a band 1 (1.5 ppm±0.2 ppm), a band 2 (2.3 ppm±0.2 ppm), and a band 4 (2.7 ppm±0.2 ppm) are selected as suppression targets. In this manner, in a single MRS pulse sequence, multiple frequency bands may be selected as suppression targets.

The combination of frequency bands selected as suppression targets in MRS pulse sequences included in a single set may be encoded by any combination of frequency bands that can be individually restored. In other words, it may be any combination for which an inverse matrix exists if "on" and "off" of the table shown in FIG. 6 are respectively represented by "1" and "0".

Next, a process of estimating a relative amount of a molecule based on an MRS signal shown at step S205 will be described in detail.

Multiple MRS signals are generated by, for example, adding, through the estimating function 513, multiple MRS signals acquired by MRS pulse sequences in which an identical frequency band is selected as a suppression target, and generating a single MRS signal relating to the frequency band. At this time, the addition may be performed after executing a phase correction process on the acquired multiple MRS signals. Thereby, deterioration in the MRS signal can be reduced.

The MRS signal can be considered to be a sum of products of signal values of the respective molecules, and can be expressed, for example, by the following Formula (1):

$$S(f,k) = \Sigma_i w_i P(i,k,TE) + n \quad (1)$$

where f represents a frequency (in units of ppm), k represents an index (e.g., #1, #2, etc.) of the MRS pulse sequence, i represents an index of the molecule type, P represents a known frequency pattern of the molecule, w represents a signal intensity to be calculated, and n represents noise.

There are some molecules that have peaks at multiple different frequencies on a spectrum due to J-coupling. For example, signals of multiple molecules that have peaks at frequency bands in the periphery of 2 ppm, the periphery of 3 ppm, the periphery of 4 ppm, etc. may exist in a mixed manner. By solving the MRS signal obtained by each MRS pulse sequence using, for example, non-linear regression through the MRS pulse sequence acquisition method according to the present embodiment, it is possible to calculate a relative amount of a desired molecule existing in a measurement target region.

The configuration is not limited to being solved analytically, and calculation may be performed based on a machine learning model.

An example of a molecule relative amount estimation process using a machine learning model will be described with reference to FIGS. 7 and 8.

FIG. 7 is a diagram showing a learning stage of a machine learning model.

The training function 515 causes a network model 702 to learn by taking, as input data, two or more spectral signals calculated based on a sum of products of basis spectrums of multiple molecules, and using a relative amount of each of the molecules as ground truth data. The basis spectrums of the molecules can be generated from, for example, an MRS signal acquired using a phantom relating to a single molecule. By executing a signal synthesis process 701 on basis spectrums of multiple different molecules, two or more spectral signals to be used as input data are generated.

The signal synthesis process 701 performs a multiple-accumulate operation on the basis spectrums of multiple different molecules based on Formula (1). This can be achieved by, for example, simulating an MRS pulse sequence in which two different frequency bands are selected as suppression targets, and an MRS pulse sequence in which a broad frequency band is specified, and generating three spectral signals including basis spectrums of multiple different molecules. If TEs (echo times) at the time of acquisition of basis spectrums of multiple different molecules do not match, a correction formula of TE-dependent basis spectrums can be calculated in advance. At the time of generating a spectral signal, basis spectrums can be corrected to make the TEs match, and then a multiply-accumulate operation can be performed in the signal synthesis process 701.

To increase the robustness at the time of inference, the processing circuitry may be configured to perform a multiply-accumulate operation through the training function 515 by randomly setting values of each of the magnitude of a signal intensity w to be calculated, a peak of a known frequency pattern P of a molecule, and a noise n, thereby generating a spectral signal.

For the network structure and the learning method of the network model 702, a method of minimizing the loss function by error back-propagation using, for example, a neural network, a convolutional neural network, etc. may be used. The network structure and the learning method are not limited thereto, and any network structure and learning method that may be used in supervised learning or self-supervised learning in a regression task may be adopted. Upon completion of the learning after satisfaction of predetermined completion conditions, if the loss function has become equal to or lower than a threshold value, the learning is completed, and the trained model 703 is generated.

Next, an inference stage of the machine learning model will be described with reference to FIG. 8.

Through the estimating function 513, the processing circuitry 51 is configured to input acquired multiple MRS signals to the generated trained model 703, and to output, from the trained model 703, relative amounts of one or more molecules included in the measurement target region.

In the example of FIG. 8, the processing circuitry 51 estimates, through the estimating function 513, a relative amount of each molecule, for example, estimates a relative amount of molecule 1 (e.g., NAA (N-Acetyl-L-aspartic Acid)=107.5) and a relative amount of molecule 2 (e.g., GABA (gamma-aminobutylic acid)=15.3) by inputting an MRS signal #1, an MRS signal #2, and an MRS signal #3 with different frequency bands as suppression targets, which have been obtained through the obtaining function 512, to the trained model 703.

Herein, an MRS signal (spectral signal) is assumed; however, the configuration is not limited thereto, and MRSk data, which is k-space data, may be taken as an input. In the case of employing MRS k data as an input of the trained model 703, the network model 702 can be trained by taking, as input data, MRSk data generated from spectral data calculated by a multiply-accumulate operation of multiple basis spectrums.

Also, learning relating to an unknown molecule may be incorporated. For example, a relative amount of an unknown molecule is added in a certain amount to the ground truth data, in addition to the relative amounts of known molecules to be input. By allowing a total value to be output as an inference result, it is possible to infer, from the total value, that the remaining relative amount obtained by subtracting the inferred relative amount from the total value can be inferred to be "unclassified (others)".

The MRS pulse sequence signals to be input to the trained model 703 may have different resolutions. For example, signals with different resolutions, such as an MRS signal #1 with a 3×3×3 voxel size and an MRS signal #2 with a 1.5×1.5×1.5 voxel size may be taken as inputs.

Moreover, a differential signal may be further input to the trained model 703. For example, at the time of learning of the network model 702, a differential signal between a spectral signal corresponding to the MRS pulse sequence #1 and a spectral signal corresponding to the MRS pulse sequence #2 may be taken as input data for further learning. This can be achieved by inputting, at the inference stage, a differential signal "MRS signal #1-MRS signal #2" to the trained model 703, in addition to the MRS signal #1, the MRS signal #2, and the MRS signal #3.

Next, a first example of a user interface that accepts a frequency band input at step S201 will be described with reference to FIG. 9.

Figure 9:
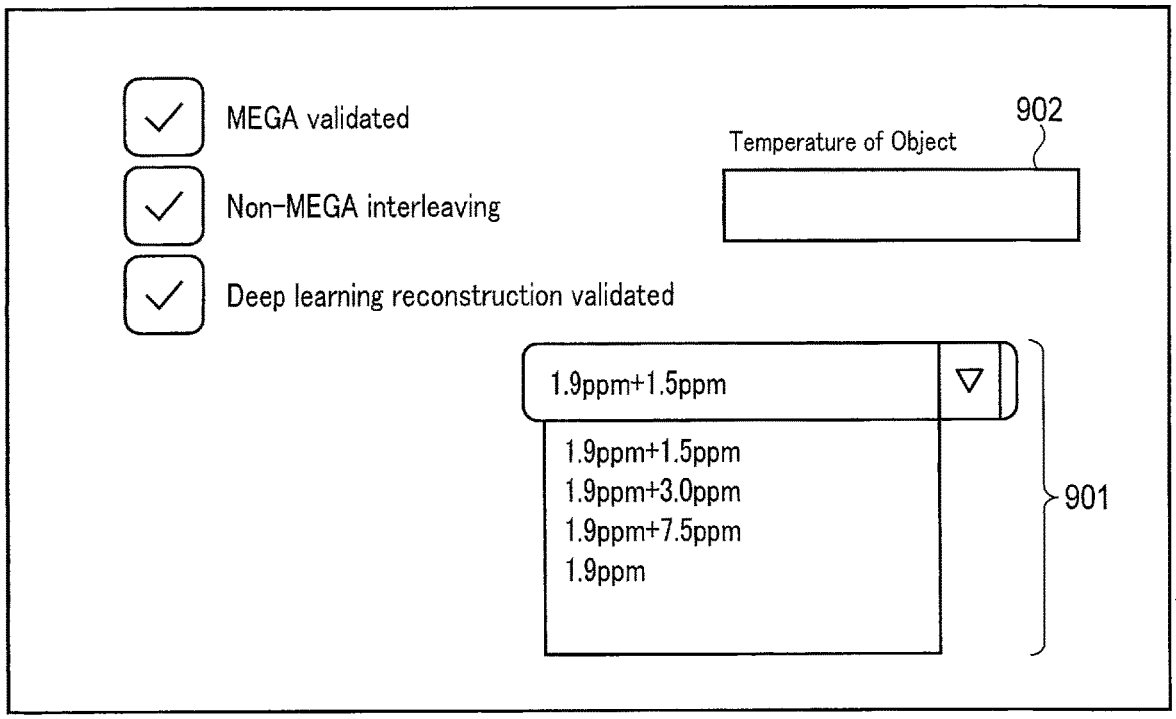
FIG. 9 is a diagram showing a first example of a user interface that accepts a frequency band input.

The example of FIG. 9 shows a user interface that allows a process to be validated upon checking of a checkbox indicating what MRS pulse sequence is to be employed. If a trained model is applied, it is assumed herein that the checkbox "Deep learning reconstruction" is checked. The display control function 514 causes a window 901 to display one or more predetermined frequency band candidates for selection as a suppression target.

Specifically, if the window 901 is specified, one or more frequency band candidates that can be selected as suppression targets are displayed in a pull-down list. That is, a set of frequency bands set at the time of generation of the trained model is displayed. In the example of FIG. 9, it is assumed that the MRS signal #3 of all the frequency bands is used. The remaining frequency bands are selected as suppression targets, and a set of frequency bands that can be selected as suppression targets is displayed, such as "1.9 ppm+1.5 ppm", indicating that the periphery of 1.9 ppm and the periphery of 1.5 ppm are selected as suppression targets, and "1.9 ppm+3.0 ppm", indicating that the periphery of 1.9 ppm and the periphery of 3.0 ppm are selected as suppression targets.

Also, an input field 902 that accepts an input of a temperature of an object is displayed on the user interface. If a temperature value is input to the input field 902, the chemical shift value of water (e.g., on the order of 4.6 ppm to 5.0 ppm) can be treated as a value that fits the accepted temperature.

Next, a second example of a user interface that accepts a frequency band input will be described with reference to FIG. 10.

Figure 10:
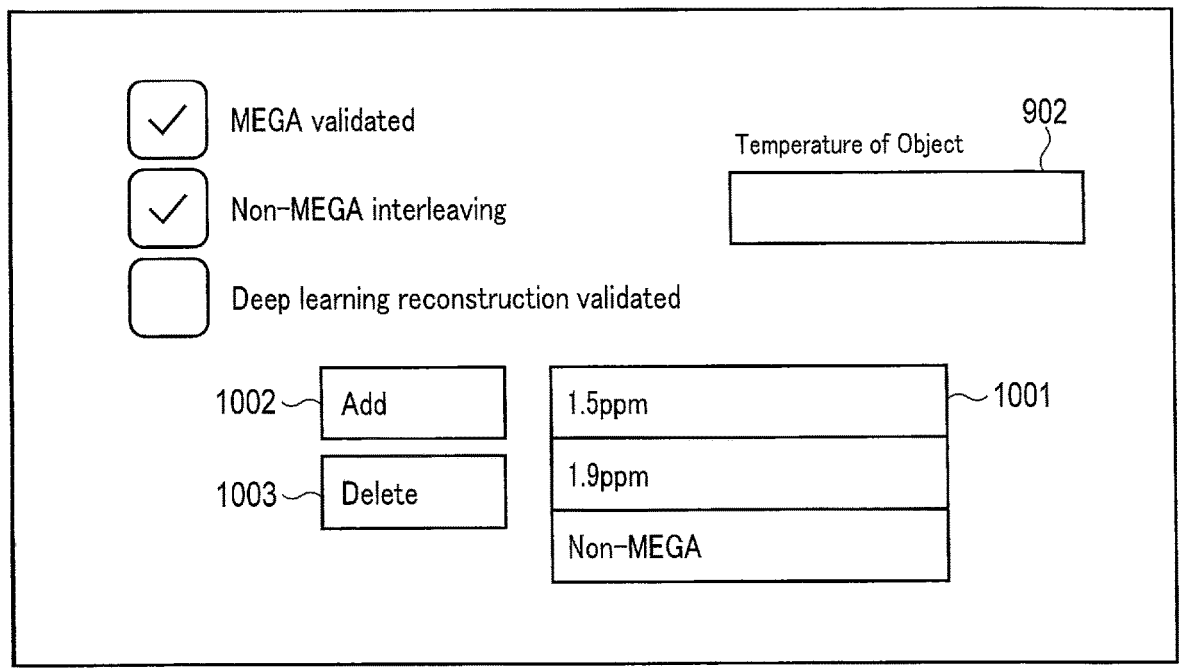
FIG. 10 is a diagram showing a first example of a user interface that accepts a frequency band input.

FIG. 10 is similar to FIG. 9; however, a case is assumed where a trained model is not applied. That is, a case is assumed where the checkbox "Deep learning reconstruction" is not checked. If a trained model is not applied, since the frequency bands are not restricted to those learned with a trained model, the display control function 514 causes the screen to display one or more frequency band candidates that allow for data reconstruction for input or selection as suppression targets. Specifically, on a window 1001, a frequency band value to be selected may be manually input by the user, or a selective input may be made in a pull-down list, etc. In the case of inputting the frequency band value, a frequency region to be selected may be confirmed by pressing down an add button 1002. Also, a frequency band to be selected may be deleted by pressing down a delete button 1003.

It is also possible to set a window via which a desired molecule that the user wishes to detect can be input, and if information relating to the molecule is input via the window, a frequency band to be selected as a suppression target may be preset based on, for example, information on the basis spectrum inherent in the molecule used at the time of training of a trained model, although illustration of such a configuration is omitted.

According to the present embodiment described above, two or more MRS pulse sequences in which different frequency bands are selected as suppression targets are generated, and a relative amount of each molecule included in the measurement target region is estimated, based on a co-occurrence of a molecule-type-dependent frequency profile from an MRS signal obtained in each MRS pulse sequence. Thereby, even if MRS signals of multiple molecules overlap, or a desired signal is weak and buried by other signals, it is possible to increase visual recognizability of the signal of the molecule. It is thereby possible to improve, for example, the precision of molecule discrimination.

The term "processor" used herein refers to, for example, circuitry such as a central processing unit (CPU), a graphics processing unit (GPU), an application-specific integrated circuit (ASIC), or a programmable logic device (e.g., simple programmable logic device (SPLD), a complex programmable logic device (CPLD), or a field programmable gate array (FPGA)). If the processor is, for example, a CPU, the processor reads and executes programs stored in storage circuitry to implement the functions. If the processor is, for example, an ASIC, the functions are directly incorporated in the circuitry of the processor as logic circuitry, instead of the programs being stored in the storage circuitry. Each processor in the present embodiment is not limited to a single circuitry-type processor, and multiple independent circuits may be combined and integrated as a single processor to realize the intended functions. Furthermore, the functions may be implemented by a single processor into which multiple components shown in the drawings are incorporated.

In addition, the functions according to the embodiment may be implemented by installing a program for executing the process into a computer such as a workstation and expanding the program on the memory. At this time, the program capable of causing the computer to execute such an approach may be stored in a storage medium such as a magnetic disk (hard disk), an optical disk (a CD-ROM, a DVD, etc.), a semiconductor memory, etc. and distributed.

While certain embodiments have been described, they have been presented by way of example only, and are not intended to limit the scope of the inventions. The embodiments described herein may be embodied in a variety of other forms; furthermore, various omissions, substitutions, changes or combinations of the embodiments may be made without departing from the spirit of the inventions. The embodiments and their modifications are included in the scope and spirit of the invention and are included in the scope of the claimed inventions and their equivalents.

Regarding the foregoing embodiments, the appendage of the following is disclosed as one aspect and selective features of the invention.

<1> A data processing apparatus includes processing circuitry. The processing circuitry generates two or more magnetic resonance spectroscopy (MRS) pulse sequences in which different frequency bands are selected as suppression targets; The processing circuitry obtains multiple MRS signals acquired by the two or more MRS pulse sequences. The processing circuitry estimates a relative amount of each molecule included in a measurement target region from the MRS signals, based on a co-occurrence of a frequency profile that depends on a molecule type.

<2> Each of the MRS pulse sequences may include a frequency selection pulse for selecting a frequency band corresponding to multiple different frequency profile as a suppression target.

<3> The processing circuitry may further generate an MRS pulse sequence not including the frequency selection pulse. The processing circuitry may further obtain an MRS signal by the MRS pulse sequence not including the frequency selection pulse.

<4> The frequency selection pulse may be a MEGA pulse or a frequency-selective pre-pulse.

<5> The two or more MRS pulse sequences including the frequency selection pulse may have an overlapped part of frequency band.

<6> The MRS pulse sequences may excite multiple frequency bands at once.

<7> The MRS signals may be obtained by repeatedly executing multiple sets of pulse sequences, the multiple sets each including the two or more MRS pulse sequences.

<8> The processing circuitry may input each of the MRS signals into a trained model to output a relative amount of one or more molecules included in the measurement target region, the trained model obtained by training a model by taking, as input data, a spectral signal that is based on a sum of products of basis spectrums of multiple molecules and a relative amount of each of the multiple molecules as ground truth data.

<9> The processing circuitry may input a differential signal to the trained model, the differential signal being a difference between a first MRS signal and a second MRS signal, the first MRS signal and the second MRS signal being included in the MRS signals.

<10> The processing circuitry may further cause a screen to display one or more predetermined frequency band candidates for selection as suppression targets if the trained model is applied.

<11> The processing circuitry may further cause a screen to display one or more frequency band candidates that allow for data reconstruction for input or selection as suppression targets if a trained model is not applied.

<12> A data processing method includes: generating two or more magnetic resonance spectroscopy (MRS) pulse sequences in which different frequency bands are selected as suppression targets; obtaining multiple MRS signals acquired by the two or more MRS pulse sequences; and estimating a relative amount of each molecule included in a measurement target region from the MRS signals, based on a co-occurrence of a frequency profile that depends on a molecule type.

<13> A data processing program causes a computer to implement: a generating function of generating two or more magnetic resonance spectroscopy (MRS) pulse sequences in which different frequency bands are selected as suppression targets; an obtaining function of obtaining multiple MRS signals acquired by the two or more MRS pulse sequences; and an estimating function of estimating a relative amount of each molecule included in a measurement target region from the MRS signals, based on a co-occurrence of a frequency profile that depends on a molecule type.

<14> A magnetic resonance imaging apparatus includes processing circuitry and an acquiring unit. The processing circuitry generates two or more magnetic resonance spectroscopy (MRS) pulse sequences in which different frequency bands are selected as suppression targets. The acquiring unit transmits an RF signal based on the two or more MRS pulse sequences, and acquires multiple MRS signals respectively corresponding to the MRS pulse sequences from a measurement target region. The processing circuitry estimates a relative amount of each molecule included in the measurement target region from the MRS signals, based on a co-occurrence of a frequency profile that depends on a molecule type.

What is claimed is:

1. A data processing apparatus, comprising:
processing circuitry configured to:
generate two or more magnetic resonance spectroscopy (MRS) pulse sequences in which different frequency bands are selected as suppression targets;
obtain multiple MRS signals acquired by the two or more MRS pulse sequences; and
estimate a relative amount of each molecule included in a measurement target region from the MRS signals, based on a co-occurrence of a frequency profile that depends on a molecule type.

2. The data processing apparatus according to claim 1, wherein each of the MRS pulse sequences includes a frequency selection pulse for selecting a frequency band corresponding to multiple different frequency profiles.

3. The data processing apparatus according to claim 2, wherein the processing circuitry is further configured to:
generate a particular MRS pulse sequence not including the frequency selection pulse, and
obtain a particular MRS signal by the particular MRS pulse sequence not including the frequency selection pulse.

4. The data processing apparatus according to claim 2, wherein the frequency selection pulse is a MEGA pulse or a frequency-selective pre-pulse.

5. The data processing apparatus according to claim 2, wherein the two or more MRS pulse sequences including the frequency selection pulse have an overlapped part of a frequency band.

6. The data processing apparatus according to claim 1, wherein the MRS pulse sequences excite multiple frequency bands at once.

7. The data processing apparatus according to claim 1, wherein
the MRS signals are obtained by repeatedly executing multiple sets of pulse sequences, the multiple sets of pulse sequences each including the generated two or more MRS pulse sequences.

8. The data processing apparatus according to claim 1, wherein the processing circuitry is further configured to input each of the MRS signals into a trained model to output a relative amount of one or more molecules included in the measurement target region, the trained model obtained by training a model by taking, as input data, a spectral signal that is based on a sum of products of basis spectrums of multiple molecules and taking, as ground truth data, a relative amount of each of the multiple molecules.

9. The data processing apparatus according to claim 8, wherein the processing circuitry is further configured to input a differential signal to the trained model, the differential signal being a difference between a first MRS signal and a second MRS signal, the first MRS signal and the second MRS signal being included in the MRS signals.

10. The data processing apparatus according to claim 8, wherein the processing circuitry is further configured to cause a screen to display one or more predetermined frequency band candidates for selection if the trained model is applied.

11. The data processing apparatus according to claim 1, wherein the processing circuitry is further configured to cause a screen to display one or more frequency band candidates that allow for data reconstruction for input or selection if a trained model is not applied.

12. A data processing method comprising:
generating two or more magnetic resonance spectroscopy (MRS) pulse sequences in which different frequency bands are selected as suppression targets;
obtaining multiple MRS signals acquired by the two or more MRS pulse sequences; and
estimating a relative amount of each molecule included in a measurement target region from the MRS signals, based on a co-occurrence of a frequency profile that depends on a molecule type.

13. A magnetic resonance imaging apparatus, comprising:
processing circuitry; and
an acquiring unit,
wherein the processing circuitry generates two or more magnetic resonance spectroscopy (MRS) pulse sequences in which different frequency bands are selected as suppression targets,
the acquiring unit transmits an RF signal based on the two or more MRS pulse sequences, and acquires multiple MRS signals respectively corresponding to the MRS pulse sequences from a measurement target region, and
the processing circuitry estimates a relative amount of each molecule included in the measurement target region from the MRS signals, based on a co-occurrence of a frequency profile that depends on a molecule type.

* * * * *